US010513733B2

(12) United States Patent
Georgiou et al.

(10) Patent No.: US 10,513,733 B2
(45) Date of Patent: Dec. 24, 2019

(54) HIGH THROUGHOUT SEQUENCING OF PAIRED VH AND VL TRANSCRIPTS FROM B CELLS SECRETING ANTIGEN-SPECIFIC ANTIBODIES

(71) Applicant: BOARD OF REGENTS, THE UNIVERSITY OF TEXAS SYSTEM, Austin, TX (US)

(72) Inventors: George Georgiou, Austin, TX (US); Erik L. Johnson, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 508 days.

(21) Appl. No.: 15/078,507

(22) Filed: Mar. 23, 2016

(65) Prior Publication Data
US 2016/0319348 A1 Nov. 3, 2016

Related U.S. Application Data

(60) Provisional application No. 62/136,690, filed on Mar. 23, 2015.

(51) Int. Cl.
| C12Q 1/68 | (2018.01) |
| C12Q 1/6874 | (2018.01) |
| C12Q 1/6804 | (2018.01) |
| C12Q 1/6806 | (2018.01) |
| C12Q 1/6869 | (2018.01) |

(52) U.S. Cl.
CPC ......... *C12Q 1/6874* (2013.01); *C12Q 1/6804* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| 9,090,674 | B2 | 7/2015 | Reddy et al. |
| 9,146,241 | B2 | 9/2015 | Lavinder et al. |
| 9,304,065 | B2 | 4/2016 | Fowler et al. |
| 2005/0272039 | A1 | 12/2005 | Yasuda |
| 2006/0233812 | A1 | 10/2006 | Burnie et al. |

(Continued)

FOREIGN PATENT DOCUMENTS

| GB | 2502577 | 4/2013 |
| JP | 2004-81084 | 3/2004 |

(Continued)

OTHER PUBLICATIONS

Arnaout, "Specificity and overlap in gene segment-defined antibody repertoires," *BMC Genomics*, 6:148, 2005.

(Continued)

*Primary Examiner* — Samuel C Woolwine
(74) *Attorney, Agent, or Firm* — Parker Highlander PLLC (57) ABSTRACT

Methods for determining the VH:VL antibody repertoire from cells, such as antigen-specific B cells, in a high throughput manner. In some aspects, methods are provided for the capture of mRNA transcripts from single B cells that secreted antigen-specific antibodies followed by sequencing of the corresponding cDNAs encoding antibody VH and VL sequences. Libraries of antibodies produced by such methods are also provided.

19 Claims, 3 Drawing Sheets

(56) References Cited

U.S. PATENT DOCUMENTS

| | | |
|---|---|---|
| 2007/0172887 A1 | 7/2007 | Takacs et al. |
| 2007/0281313 A1 | 12/2007 | Taniguchi et al. |
| 2009/0098555 A1 | 4/2009 | Roth et al. |
| 2011/0312505 A1 | 12/2011 | Reddy et al. |
| 2012/0308555 A1 | 12/2012 | Polakiewicz et al. |
| 2012/0312505 A1 | 12/2012 | Youbi-Idrissi |
| 2013/0178370 A1 | 7/2013 | Lavinder et al. |
| 2014/0057799 A1 | 2/2014 | Johnson |
| 2015/0141261 A1 | 5/2015 | Hunicke-Smith et al. |
| 2016/0034639 A1 | 2/2016 | Reddy et al. |
| 2016/0146830 A1 | 5/2016 | Lavinder et al. |

FOREIGN PATENT DOCUMENTS

| | | | |
|---|---|---|---|
| JP | 2007-505611 | 3/2007 | |
| JP | 2007-319028 | 12/2007 | |
| JP | 2009-284834 | 12/2009 | |
| JP | 2010-535150 | 11/2010 | |
| WO | WO 03/052416 | 6/2003 | |
| WO | WO 2005/042774 | 5/2005 | |
| WO | WO 2005/084134 | 9/2005 | |
| WO | WO 2008/079914 | 7/2008 | |
| WO | WO 2008/104184 | 9/2008 | |
| WO | WO 2009/100896 | 8/2009 | |
| WO | WO 2010/083456 | 7/2010 | |
| WO | WO 2011/146514 | 11/2011 | |
| WO | WO 2012/061412 | 5/2012 | |
| WO | WO 2012/072705 | 6/2012 | |
| WO | WO 2012/083225 | 6/2012 | |
| WO | WO-2013188872 A1 * | 12/2013 | ........... C12Q 1/6806 |

OTHER PUBLICATIONS

Behrendt et al., "The role of somatic mutation in determining the affinity of anti-DNA antibodies," *Clin Exp Immunol*, 131:182-189, 2003.

Boudinot et al., "New perspectives for large-scale repertoire analysis of immune receptors," *Molecular Immunology*, 45:2437-2445, 2008.

Boyd et al., "Measurement and clinical monitoring of human lymphocyte clonality by massively parallel V-D-J pyrosequencing," *Science Translational Medicine*, 1(12):12ra23, 2009.

Burgoon et al., "Laser-capture microdissection of plasma cells from subacute sclerosing panencephalitis brain reveals intrathecal disease-relevant antibodies," PNAS, 102(20):7245-7250, 2005.

Campbell et al., "Subclonal phylogenetic structures in cancer revealed by ultra-deep sequencing," *PNAS*, 105(35):13081-13086, 2008.

Chapal et al., "Thyroid libraries contain the peroxidase autoantibodies obtained from random single chain Fv libraries contain the same heavy/light chain combinations as occur in vivo," *Endocrinology*, 142(11):4740-4750, 2001.

Cheung et al., "A proteomics approach for the identification and cloning of monoclonal antibodies from serum", *Nature Biotechnology*, 30(5):447-52, 2012.

Clackson et al., "Making antibody fragments using phage display libraries," *Letters to Nature*, 352:624-628, 1991.

Correia-Neves et al., "The shaping of the T cell repertoire," *Immunity*, 14:21-32, 2001.

Damoc et al., "High resolution proteome analysis of cryoglobulins using Fourier transform-ion cyclotron resonance mass spectrometry", *Proteomics*, 3:1425-1433, 2003.

De Costa et al., "Sequencing and quantifying IgG fragments and antigen-binding regions by mass spectrometry," *Journal of Proteome Research*, 9:2937-2945, 2010.

DeKosky et al., "High-throughput sequencing of the paired human immunoglobulin heavy and light chain repertoire", *Nature Biotechnology*, 31(2):166-169, 2013.

Dornmair et al., "Novel approaches for identifying target antigens of autoreactive human B and T cells", *Seminars in Immunopathology*, 31(4):467-477, 2009.

Extended European Search Report issued in European Application No. 11784105.6, dated Sep. 11, 2013.

Fischer et al., "Sequencing antibody repertoires: the next generation", *MAbs*, 3(1):17-20, 2011.

Freeman et al., "Profiling the T-cell receptor beta-chain repertoire by massively parallel sequencing," *Genome Research*, 19:1817-1824, 2009.

Glanville et al., "Precise determination of the diversity of a combinatorial antibody library gives insight into the human immunoglobulin repertoire", *Proc Natl Acad Sci USA*, 106(48):20216-20221, 2009.

Huse et al., "Purification of antibodies by affinity chromatography", *J Biochem Biophys Methods*, 51:217-231, 2002.

Instructions for Product Nos. 21901 and 21902, Maleimide-PEG2-Biotin Sulfhydryl-reactive biotin labeling reagent with polyethylene glycol (PEG) spacer arm, published by Thermo Fisher Scientific, Inc., 2008.

International Invitation to Pay Additional Fees issued in International Application No. PCT/US2013/046130, dated Sep. 4, 2013.

International Preliminary Report on Patentability issued in International Application No. PCT/US2013/046130, dated Dec. 24, 2014.

International Search Report and Written Opinion issued in International Application No. PCT/US2013/046130, dated Nov. 15, 2013.

Ippolito et al., "Antibody repertoires in humanized NOD-scid-IL2Rγ(null) mice and human B cells reveals human-like diversification and tolerance checkpoints in the mouse", *PLoS One*, 7(4):e35497, 2012.

Kurokawa et al., "Paired cloning of the T cell receptor α and β genes from a single T cell without the establishment of a T cell clone," *Clin Exp Immunol*, 123:340-345, 2001.

Maiolica et al., "Targeted proteome investigation via selected reaction monitoring mass spectrometry", *Journal of Proteomics*, 75(12):3495-3513, 2012.

Matsutani et al., "Restricted usage of T-cell receptor α-chain region (TCRAV) and T-cell receptor β-chain variable region (TCRBV) repertoires after human allogeneic haematopoietic transplantation," *British Journal of Haematology*, 109:759-769, 2000.

McMahan et al., "Production, characterization, and immunogenicity of a soluble rat single chain T cell receptor specific for an encephalitogenic peptide," *The Journal of Biological Chemistry*, 278(33):30961-30970, 2003.

Meijer et al., "Isolation of human antibody repertoires with preservation of the natural heavy and light chain pairing", *Journal of Molecular Biology*, 358(3): 764-772, 2006.

Meijer et al., "Isolation of human repertoires with preservation of the natural heavy and light chain pairing", *Journal of Molecular Biology*, 358(3): 764-772, 2006. (Supplementary Data).

Mouquet et al., "Complex-type N-glycan recognition by potent broadly neutralizing HIV antibodies", *Proc Natl Acad Sci USA*, 109(47):E3268-E3277, 2012.

Nazabal et al., "Immunoassays with direct mass spectrometric detection", *Analytical Chemistry*, 78(11):3562-3570, 2006.

Obermeier et al., "Matching of oligoclonal immunoglobulin transcriptomes and proteomes of cerebrospinal fluid in multiple sclerosis," *Nature Medicine*, 14(6):688-693, 2008.

Office Communication issued in corresponding European Application No. 13733180.7, dated Sep. 24, 2015.

Omenn et al., "Overview of the HUPO plasma proteome project: results from the pilot phase with 35 collaborating laboratories and multiple analytical groups, generating a core dataset of 3020 proteins and a publicly-available database", *Proteomics*, 5:3226-3245, 2005.

Omenn et al., "Overview of the HUPO plasma proteome project: results from the pilot phase with 35 collaborating laboratories and multiple analytical groups, generating a core dataset of 3020 proteins and a publicly-available database", *Proteomics*, 5:3226-3245, 2005. [Supplementary Materials, Protein dataset].

Packer and Muraro, "Optimized clonotypic analysis of T-cell receptor repertoire in immune reconstitution," *Experimental Hematology*, 35:516-521, 2007.

PCT International Search Report issued in International Application No. PCT/US2011/036852, dated Sep. 26, 2012.

PCT Third Party Observation submitted in International Application No. PCT/US2011/036852 dated Sep. 14, 2012.

(56) References Cited

OTHER PUBLICATIONS

PCT International Search Report and Written Opinion issued in International Application No. PCT/US2012/066454, dated Jul. 31, 2013.
Peng, "Protein mixture analysis by tandem mass spectrometry" In: The Bioinformatics of Brains: From Genes and Proteins to Behaviors (Williams RW, ed.), pp. 61-68 (2003), Washington, DC: Society for Neuroscience.
Persson et al., "Generation of diverse high-affinity human monoclonal antibodies by repertoire cloning," *Proc. Natl. Acad. Sci. USA*, 88:2432-2436, 1991.
Ravetch et al., "Structure of the human immunoglobulin mu locus: characterization of embryonic and rearranged J and D genes", *Cell*, 27:583-591, 1981.
Reddy et al., "Monoclonal antibodies isolated without screening by analyzing the variable-gene repertoire of plasma cells", *Nature Biotechnology*, 28(9):965-9, 2010.
Sato et al., "Proteomics-directed cloning of circulating antiviral human monoclonal antibodies", *Nature Biotechnology*, 30(11):1039-1043, 2012.
Schluter et al., "Sequence analysis of homogeneous peptides of shark immunoglobin light chains by tandem analysis mass spectrometry: correlation with gene sequence and homologies among variable and constant region peptides of sharks and mammals," *Molecular Immunology*, 27(1):17-23, 1990.

Tanaka et al., "Single-cell analysis of T-cell receptor repertoire of HTLV-1 tax-specific cytoxic T-cells in allogeneic transplant recipients with adult T-cell leukemia/lymphoma", *Cancer Research*, 70(15): 6181-6192, 2010.
Weinstein et al., "High-throughput sequencing of the zebrafish antibody repertoire," *Science*, 324:807-810, 2009.
Willis et al., "Rapid molecular cloning of rearrangements of the IGHJ locus using long-distance inverse polymerase chain reaction", *Blood*, 90(6):2456-2464, 1997.
Wine et al., "Molecular deconvolution of the monoclonal antibodies that comprise the polyclonal serum response", *Proc Natl Acad Sci USA*, 110(8):2993-2998, 2013.
Yates, "Mass spectrometry from genomics to proteomics", *Trends Genet.*, 16(1):5-8, 2000.
Kumaresan et al., "High-throughput single copy DNA amplification and cell analysis in engineered nanoliter droplets," *Analytical Chemistry*, 80 (10):3522-3529, 2008.
Mary et al., "Analysis of gene expression at the single-cell level using microdroplet-based microfluidic technology," *Biomicrofluidics*, 5:024109, 2011.
Novak et al., "Single-cell multiplex gene detection and sequencing with microfluidically generated agarose emulsions," *Angew. Chem. Int. Ed.*, 50:390-395, 2011.
Zhang et al., "Massively parallel single-molecule and single-cell emulsion reverse transcription polymerase chain reaction using agarose droplet microfluidics," *Analytical Chemistry*, 84:3599-3605, 2012.

* cited by examiner

HIGH THROUGHOUT SEQUENCING OF PAIRED VH AND VL TRANSCRIPTS FROM B CELLS SECRETING ANTIGEN-SPECIFIC ANTIBODIES

CROSS-REFERENCE TO RELATED APPLICATIONS

This application claims the benefit of U.S. Provisional Patent Application No. 62/136,690, filed Mar. 23, 2015, the entirety of which is incorporated herein by reference.

STATEMENT OF FEDERAL FUNDING

The invention was made with government support under Grant No. HDTRA1-12-C-0105 awarded by the United States Department of Defense. The government has certain rights in the invention.

BACKGROUND OF THE INVENTION

1. Field of the Invention

The present invention relates generally to the field of molecular biology and immunology. More particularly, it concerns methods for high-throughput isolation cDNAs encoding immune cell receptors and antibodies.

2. Description of Related Art

There is a need to identify the expression of two or more transcripts from individual B cells expressing antigen-specific antibodies at high throughput (Bardelli et al. 2013, Love et al. 2006, Mazutis et al. 2013, Smith et al. 2009, Ogunniyi et al. 2009). In particular, for numerous biotechnology and medical applications it is important to identify and sequence the gene pairs encoding the two chains comprising adaptive immune receptors from individual cells at a very high throughput in order to accurately determine the complete repertoires of immune receptors expressed in patients or in laboratory animals. Immune receptors expressed by B lymphocytes are encoded by the VH and VL antibody genes. Humans have many tens of thousands or millions of distinct B cells. High-throughput DNA sequencing technologies have been used to determine repertoires of VH or VL chains of relevance to particular disease states or, more generally, to study the function of the adaptive immune system (Wu et al., 2011). Immunology researchers have an especially great need for high throughput analysis of multiple transcripts at once (DeKosky et al. 2013, Georgiou et al. 2014)

Currently available methods for immune repertoire sequencing involve mRNA isolation from a cell population of interest, e.g., memory B-cells or plasma cells from bone marrow, followed by RT-PCR in bulk to synthesize cDNA for high-throughput DNA sequencing (Reddy et al., 2010; Krause et al., 2011). However, heavy and light antibody chains (or α and β T-cell receptors) are encoded on separate mRNA strands and must be sequenced separately. Of particular interest is the determination of the sequences of VH and VL genes encoded by single B cells that express antibodies specific to a desired antigen. Without multiple-transcript analysis at the single-cell level to collect heavy and light chain pairing data from B cells expressing antigen-specific antibodies, the full adaptive immune receptor, which includes both chains, cannot be sequenced or reconstructed and expressed for further study.

SUMMARY OF THE INVENTION

In a first embodiment the invention provides a method for identifying the sequence of two or more transcripts from a plurality of single cells comprising incubating isolated single cells and capture agents in individual compartments, wherein the capture agents bind to both mRNA and antibodies, lysing the isolated cells, contacting the capture agents, along bound mRNA and antibodies, with affinity agents that bind to antibodies to form complexes, purifying the complexes, performing reverse transcription and PCR amplification on individual complexes to generate linked amplification products comprising two or more cDNAs from said cell, and sequencing amplification products to identify antibody sequences from a single cell. In some aspects, the method is further defined as a method for obtaining antibody sequences from a plurality of individual B cells. In further aspects, the individual B cells are primary B-cells from a human subject. In some aspects, the method is further defined as a method for obtaining paired antibody VH and VL sequences for an antibody that binds to an antigen of interest.

In certain aspects, the capture agents are beads. In particular aspects, the beads are magnetic. In certain aspects, the capture agents comprise or are conjugated to a moiety that binds to antibodies, such a as a moiety that binds to an antibody constant domain or an antigen that is recognized by an antibodies. Thus, in certain aspects, the capture agents comprise the antigen of interest. In further aspects, the capture agents are beads that comprise the antigen of interest and a mRNA binding moiety. For example, the mRNA binding moiety can be a cap binding protein (e.g., eIF4e), or oligonucleotides which hybridize mRNA. In further aspects, the oligonucleotides comprise poly(T) sequences. In certain aspects, the capture agents are conjugated to a mixture of antibody and mRNA binding moieties. For example, in some aspects, the ratio of antibody and mRNA binding moieties on the captures agents are, on average, between about 1:100 and 100:1, 1:10 and 10:1, 1:5 and 5:1, 1:3 and 3:1 or 1:2 and 2:1.

In some further aspects, the affinity agents are beads. In certain aspects, the affinity agents have density that is less than the capture agents. In some particular aspects, the affinity agents comprise polystyrene beads or are magnetic beads. In further aspects, the affinity agents bind to an antibody, such as an antibody constant region. In particular aspects, the affinity agents comprise protein G or protein A. In some aspects, the affinity agents comprise a mammalian Fc-binding protein or an antibody binding portion thereof.

In some aspects, the individual compartments are wells in a gel or microtiter plate. In certain aspects, the individual compartments having a volume of less than 5 nL. In some particular aspects, the compartments are sealed with a permeable membrane prior to lysing the individual cells. In certain aspects, a method comprises incubating the cells in individual compartments in the presence of capture agents for at least 1, 2, 3, 4, 5, 6, 7, 8, 12, 16, 20, 24, 48 hours or more prior to lysis of the cells. In further aspects, lysing the cells comprises allowing a lysis solution to diffuse through the permeable membrane. In some aspects, lysing the isolated cells comprises the use of a mild detergent solution. In particular aspects, the mild detergent solution comprises a non-ionic detergent. In other aspects, the mild detergent solution comprises between about 0.1% to 5% of a polysorbate detergent.

In further aspects, the method comprises obtaining sequences from at least 10,000, 100,000 or 1,000,000 individual cells (e.g., between about 100,000 and 10 million or 100 million individual cells). Thus, in some aspects, a method comprises obtaining at least 5,000, 10,000 or 100, 000 individual paired antibody VH and VL sequences (e.g., between about 10,000 and 100,000, 1 million or 10 million individual paired sequences).

In particular aspects, purifying the complexes comprises separating complexes by physical properties. For example, complexes can be separated by the affinity, density, mass or magnetic properties. In some aspects, purifying the complexes comprises separating complexes by density. For example, the complexes may be separated by applying the complexes to a density gradient (e.g., by centrifugation on a density gradient).

In further aspects, sequencing amplification products to identify antibody sequences from a single cell comprises performing emulsion-reverse transcription and PCR amplification on individual complexes. In other aspects, this step comprises linking cDNAs by performing overlap extension reverse transcriptase polymerase chain reaction to link at least 2 transcripts into a single DNA molecule. In still further aspects, this step does not comprise the use of overlap extension reverse transcriptase polymerase chain reaction.

In some aspects, the VH and VL sequences are obtained by sequencing of distinct molecules. In certain aspects, sequestering the single cells comprises introducing the cells to a device comprising a plurality of microwells so that the majority of cells are captured as single cells. In particular aspects, the cells are mammalian cells. In further aspects, the cells are from a mammalian subject who has been exposed to an antigen of interest.

In a further embodiment, a library of antibody sequences produced by a method according to the embodiments is provided. In some aspects, the library is produced using B-cells from a human subject, said library comprising 50% to 95% of the total antibody repertoire of the subject. Thus, in still a further embodiment, there is provided a library of antibody sequences comprising 50% to 95%, 75% to 95%, 85% to 95% or 90% to 95% of the total antibody repertoire of a mammalian subject. In yet still a further embodiment there is provided a library of antigen-specific antibody sequences comprising 50% to 95%, 75% to 95%, 85% to 95% or 90% to 95% of the total antigen-specific antibody repertoire of a mammalian subject, who has been exposed to an antigen of interest.

In another further embodiment the invention provides a composition comprising an emulsion having a plurality of individual microvesicles, said microvesicles comprising primers for reverse transcription and PCR and a complex comprising (i) an affinity agents that bind to antibodies; (ii) a capture agent that binds to mRNA and antibodies; (iii) bound mRNA and (iv) bound antibodies.

Aspects of the embodiments overcome many major deficiencies in the art by providing novel methods for determining immunoglobulin sequences with some affinity and/or avidity for a designated antigen (antigen-specific sequences) in a rapid manner. For example, one object of the embodiments is to identify native heavy and light chain antibody variable pairs (VH:VL pairs) encoding for antigen-specific sequences by assaying any number of cells up to greater than 100,000 individual cells. In some preferred embodiments, between $10^4$-$10^5$ individual cells may be analyzed by methods of the embodiments.

Certain aspects of the embodiments may concern obtaining a sample from a subject (e.g., a sample comprising cells for use in the methods of the embodiments). Samples can be directly taken from a subject or can be obtained from a third party. Samples include, but are not limited to, serum, mucosa (e.g., saliva), lymph, urine, stool, and solid tissue samples. Similarly, certain aspects of the embodiments concern biological fluids and antibodies and/or nucleic acids therefrom. For example, the biological fluid can be blood (e.g., serum), cerebrospinal fluid, synovial fluid, maternal breast milk, umbilical cord blood, peritoneal fluid, mucosal secretions, tears, nasal, secretions, saliva, milk, or genitourinary secretions. In certain aspects, cells for use according to the embodiments are mammalian cells, such as mouse, rat or monkey cells. In preferred aspects the cells are human cells.

In some aspects, cells for use in the embodiments B cells, such as B cells from a selected organ, such as bone marrow. For example, the B cells can be mature B cells, such as bone marrow plasma cells, spleen plasma cells, or lymph node plasma cells, or cells from peripheral blood or a lymphoid organ. In certain aspects, B cells are selected or enriched based on differential expression of cell surface markers (e.g., Blimp-1, CD138, CXCR4, or CD45). In some cases, sequences of a selected class of antibodies are obtained, such as IgE, IgM, IgG, or IgA sequences.

In further aspects, a method of the embodiments may comprise immunizing the subject (e.g., prior to obtaining a cell sample). The method may further comprise isolation of a lymphoid tissue. The lymphoid tissue isolation may at least or about 1, 2, 3, 4, 5, 6, 6, 8, 9, 10 days or any intermediate ranges after immunization. The method may further comprise obtaining a population of nucleic acids of lymphoid tissue, preferably without separating B cells from the lymphoid tissue. The lymphoid tissue may be a primary, secondary, or tertiary lymphoid tissue, such as bone marrow, spleen, or lymph nodes. The subject may be any animal, such as mammal, fish, amphibian, or bird. The mammal may be human, mouse, primate, rabbit, sheep, or pig.

For determining the nucleic acid sequences (e.g., in the B cells or in lymphoid tissues), any nucleic acid sequencing methods known in the art may be used, including high-throughput DNA sequencing. Non-limiting examples of high-throughput sequencing methods comprise sequencing-by-synthesis (e.g., 454 sequencing), sequencing-by-ligation, sequencing-by-hybridization, single molecule DNA sequencing, multiplex polony sequencing, nanopore sequencing, or a combination thereof.

In certain embodiments, a method is provided comprising (A) isolating individual cells in a compartment with an mRNA and antibody capture agent (B) allowing for the cells to secrete antibodies for a sufficient time (C) removing the mRNA and antibody capture agent and incubating these capture agents with a second type of capture agent (an affinity agent) with affinity bearing molecules with an affinity for the secreted antibody bound to the initial mRNA and antibody capture agent (D) using various methods of enrichment for complexes of the two types of capture agents including, but not limited to, magnetic means or differences in densities (E) followed by the emulsification of these enriched capture agent complexes (F) reverse-transcription polymerase chain reaction (RT-PCR) (G), optionally, further amplification and (H) high-throughput sequencing of the amplification products.

Figure 1:
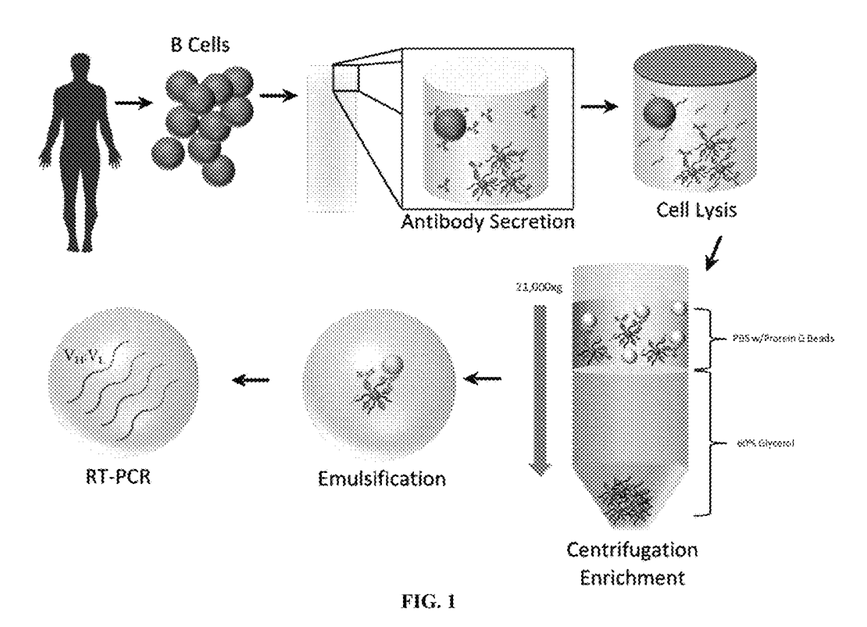
Figure 4:
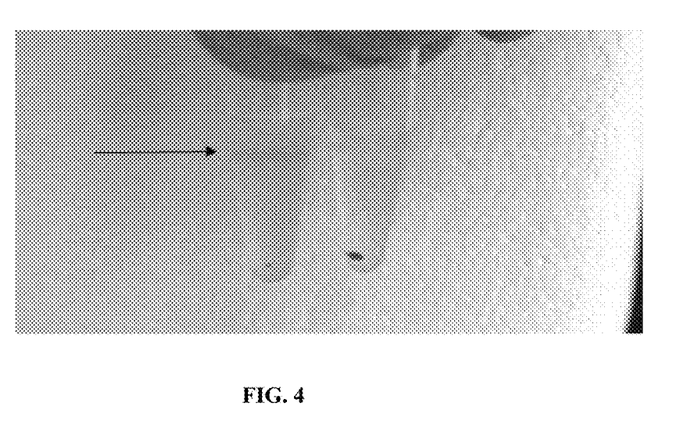
FIG. 4. Example of hybrid capture magnetic beads (derived from Dynabeads M-280 streptavidin beads) illustrating the effectiveness of enrichment of beads bound with full length anti-wtGFP hybridoma-derived antibody. The hybrid beads are those described in Examples 2 and 3. These beads were incubated with a greater than saturation level of purified anti-wtGFP hybridoma antibodies for 1 hour and then incubated for 1 hour with 3.2 micrometer (um) polystyrene Protein G coated beads. The figure depicts the results of incubating hybrid beads (left hand side) or non-hybrid only streptavidin bound Dynabead M-280 beads (right hand side, having no oligonucleotide or antigen bound) with the same amount of purified anti-wtGFP, followed by incubation with Protein G beads, followed by centrifuging over 60% glycerol for 2 minutes at 21,000×g. Streptavidin-only M-280 beads pellet, while a significant portion of hybrid capture beads remain at the interface of the glycerol layer and upper PBS layer. The interface of the glycerol and PBS layers is indicated by the arrow, while the darkly shaded layer in the left tube at this interface are the complexed beads bridged by antibodies. Note the decrease in pellet size in the left hand tube, despite the use of the same amount of beads in both reactions.

In a specific certain embodiment and shown in FIG. 1, a method is provided comprising (A) providing agents that are able to capture mRNA and secreted antibodies with an affinity and/or avidity for a desired antigen or molecule (in some preferred aspects the capture agents may comprise magnetic beads with bound oligonucleotides for mRNA capture and bound antigen) (B) isolating individual cells (e.g., of various origins and differentiation stages) in compartments along with the mRNA and antibody capture agents (C) allowing sufficient time for the cells to secrete antibodies within these compartments due to either constitutive or induced expression and subsequent secretion (D) sealing these wells with a dialysis membrane of optimal permeability and lysing these cells in situ using a lysis buffer (in some preferred aspects this lysis buffer may be a mild detergent lysis buffer) (E) isolating the mRNA and antibodies from these compartments containing individual cells using the mRNA and antibody capture agents (F) allowing this total population of retrieved capture agents to incubate with a second set of capture agents (affinity agents) bearing molecules with an affinity for the secreted antibodies (and optionally having of a lower general density than the capture agents described in (A) for a sufficient period of time to allow the capture agents to complex with each other (in some preferred embodiments this second set of capture agents may comprise polystyrene beads coated in Protein G which has a relatively high affinity for many full length antibodies of certain species) (G) followed by centrifuging to an optimal degree this incubated mixture of non-complexed beads and bead complexes over a liquid substance of a generally higher density (in some preferred embodiments, this substance may be a mixture of glycerol and water) (H) then removing the capture agent complexes at the surface of the higher density substance and leaving the non-complexed higher density capture agents below the top interface of the high density liquid layer either in a pellet form or stuck to the wall of the tube. FIG. 4 demonstrates an example of this enrichment mechanism using purified antibodies, polystyrene Protein G beads and magnetic mRNA and antibody capture agents. Next in step (I), washing the complexed capture agents bridged by antibodies in optimized buffers (in some aspects for removing any protein bound to the mRNA that might cause steric hindrance or removing any more potentially remaining ribonucleases and preparing the capture agents for subsequent amplification) (J) emulsifying these enriched capture agents in such a manner as to get one capture agent per emulsion and then performing overlap-extension RT-PCR while priming for the desired transcripts (in some preferred aspects the heavy and light chain antibody mRNAs) (K) followed by sequencing the desired amplicons representing genetic information either encoding for the antigen-specific VH:VL pair or other target genetic information carried by the cells secreting antibodies with specificity for the target antigen on the capture agent described in (A).

One object of the present embodiments is the enrichment of antibody gene sequences from B cells expressing secreting antibodies specific for antigen, while minimizing the enrichment of non-antigen specific sequences. In certain embodiments, the affinity and/or avidity of the antibodies secreted by a cell (constitutively if plasma cells or induced if memory B cells or other types of B cells of inducible differentiations), can be used to perform this enrichment of nucleic acids encoding for these cells expressing these antibodies of the desired affinity and/or avidity.

In some aspects, a bioinformatics analysis is used to minimize background noise of paired VH: VL sequences with non-specificity for the desired antigen or antigens. In some specific embodiments, hybridoma cell lines expressing and secreting a full length antibody of specificity for a known antigen may be used as cells to spike into samples as controls for determining the affinity and/or avidity specificity range of the embodiment of the invention in use, as well as the level of background mRNA mixing throughout the use of the methods.

Yet another object of the present embodiments is the enrichment of antibody variable region sequences of a broad range of affinities for a desired antigen(s), even if the antibody sequence has low affinity for the desired antigen(s). Since the present invention is assaying not only binding affinity, but the avidity effects of the antibodies (the ability of the total population of full length antibodies bound to the hybrid mRNA and antibody capture agents to allow for sufficient bridging to the second capture agent with affinity for the full length antibodies) secreted by the individual cells, even low affinity antibodies may result in the enrichment of the mRNA (in some embodiments) that encode for them. In certain embodiments, the selectivity of the enrichment for specific ranges of affinity and/or avidity of the desired population of antibodies may be modified and more tightly controlled by modifying properties of the capture agents (e.g. buoyancy of the complexed capture agents in some preferred embodiments).

In certain aspects, the mRNA and antibody hybrid capture agent may consist of various types of beads and methods of capture. For example, in some preferred embodiments, the hybrid capture agent used within the microwells for capturing both antibody and mRNA may consist of magnetic streptavidin beads bound with biotinylated antigen (containing one or multiple possible binding epitopes for assaying the specificity of the secreted antibodies) as well as biotinylated oligonucleotide-dT. In other embodiments, these mRNA and antibody hybrid capture agents may be synthesized using other methods commonly used in the art such as the use of carboxylic acid beads then conjugated to amine-containing antigen or amine-terminated capture oligonucleotides. Other bead synthesis methods are not limited to these methods alone and capture oligonucleotides might be specifically complementary to various mRNAs expressed by the cell (such as transcription factors) and may not only be oligonucleotide-dT(25) for total polyadenylated mRNA capture.

Other aspects of the present invention include the various possible methods of synthesizing and utilizing the lower density capture agent incubated with the hybrid capture agents removed from the microwells to allow for the enrichment of only complexed agents. In one embodiment these agents may be used in a non-magnetic enrichment step and may consist as previously described of low density polystyrene beads of various diameters coated in Protein G or various other molecules with affinities for various portions of full length antibodies including but not limited to anti-human Fc antibodies, anti-human Fab antibodies, anti-mouse Fc antibodies, anti-mouse light chain antibodies, anti-human light chain antibodies, Protein A, Protein L, Protein A/G or other molecules with affinity for full length antibodies secreted by human or other animal cells.

In alternative aspects of this invention, cells are encapsulated in droplets (using microfluidics or flow-focusing devices (Dekosky et al. 2015)) in optimized ratios along with the mRNA and antibody hybrid capture agents such that there is at least only one cell per emulsion droplet together with multiple capture agents. These emulsions could then be incubated for a sufficient period of time (in some preferred embodiments this may be on the level of hours or even days) to allow cells that constitutively secrete antibodies or have been induced to secrete antibodies to create a high enough concentration of antibodies within the emulsions to effectively assay the binding properties (affinity or avidity) of these antibodies to the neighboring capture agents. These emulsions could then be fused with emulsions containing a mild lysis agent to allow for single-cell mRNA capture within these emulsions. The hybrid capture agents could then be enriched in the same manner as previously described by incubating with a second lower density capture agent and centrifuging over a higher density substance at optimal speeds, followed by emulsification of the enriched capture agents in a single capture agent per single emulsion manner and followed by the usual RT-PCR and high-throughput sequencing.

In some embodiments, genetic information aside from just the heavy or light chain variable regions are of interest in combination with knowing that a cell's secreted antibodies are antigen-specific. For example, transcription factors, as previously mentioned, might provide information about the differentiation stage of the cell (such as blimp-1 or bcl-6). In addition, since plasma cells (that lack a surface receptor and in general cannot be stained with fluorescent antigen for FACS sorting), certain transcripts may provide information about whether a cell is long-lived or short-lived and may provide information about waning or protective immunity or whether they fall into various memory B cell subsets. Other endogenous or non-endogenous genes of interest that would provide information about antigen-specific cells—for example viral genes also expressed in these cells could also be of interest.

Another aspect of the invention concerns the source of the individual cells to be used in the microwell arrays. The B cells may be obtained from various sources including but not limited to humans or animals. More specifically, they may be obtained from blood, breast milk, genitourinary secretions, mucosal secretions, urine, stool and solid tissue samples (such as from tumors, bone marrow, lymph nodes, spleens, gut-associated lymphoid tissue etc.). Certain preferred animals may include but are not limited to rabbit, mouse, camels, rats, chickens and various types of primates. B cells may be also be of various differentiation stages including but not limited to memory B cells, plasmablasts and plasma cells. Often, they may involve the immunization of a subject and the isolation of B cells from the various sources previously described. In some preferred embodiments, B cells may be isolated from a human or other animal subject at various time points from the point of immunization, including but not limited to days 6, 7, 11, 14, 21 or 28 or in some cases years post-immunization.

In other embodiments, the VH:VL paired antibody sequences extracted from antigen-specific B cells using the present invention may include antibodies of various isotypes, including immunoglobulin A (IgA), immunoglobulin G (IgG), immunoglobulin E (IgE), immunoglobulin M (IgM) or immunoglobulin D (IgD) if derived from certain mammalian species including humans and mice but may include other isotypes in various other preferred species.

In certain other embodiments of the invention, the enrichment step may not be based on a difference in densities as previously described but may involve a magnetic enrichment. For example, in certain preferred embodiments, beads may be coated with antigen(s) and capture oligonucleotides and may be seeded into the microwells along with the individual cells. When these bead capture agents are removed from the microwells after cell lysis and mRNA and full length antibody capture, they may be incubated with magnetic enrichment agents such as magnetic beads of various diameters coated with various molecules possessing affinity for human or other animal full length antibodies as previously described. Complexes of the mRNA and antibody hybrid capture agents (in this case the non-magnetic silica beads) and the magnetic agent coated with Protein G or other molecules bound together are enriched preferentially and the remaining non-complexed beads carrying non-specific mRNA washed away.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 An example of the general layout of the methods. A solution of B cells from a donor is mixed with hybrid capture agent and is deposited on a slide containing a high density of single wells having a volume capable of accommodating only one cell (typically <1 nL). The B cells are allowed to settle into the wells resulting in the deposition of one cell per well based on Poisson statistics. Additionally the hybrid capture agent also settles into the wells. The B cells either secrete antibodies or are induced to secrete antibodies by administering a cytokine cocktail as established in the art (Sendra et al. 2013). The secreted antibodies are bound to the hybrid capture agent by virtue of their affinity to the antigen which is immobilized on the hybrid agent. The microwell slide is sealed with a dialysis membrane, followed by the capture of small strands of mRNA on the hybrid capture agents after diffusion of a lysis buffer through the membrane to the cell. A mixture of these collected hybrid capture agents is collected and mixed with capture agents that bear molecules with affinity for full length antibodies (depicted by the larger circles light colored circles) and layered over a 60% glycerol gradient and centrifuged, allowing hybrid capture agents without bound antibodies to pellet. A capture agent bridged by antibodies from the top layer post-centrifugation are emulsified and subjected to overlap extension RT-PCR to create amplicons of two or more transcripts.

DESCRIPTION OF ILLUSTRATIVE EMBODIMENTS

I. The Present Embodiments

The present disclosure provides identifying, correctly paired antibody heavy and light chain sequences from B cells secreting antibodies specific for a desired antigen. More particularly, methods of the present disclosure allow for the repertoire of antigen-specific antibodies in an individual organism or population of cells to be determined. Importantly, the immunoglobulin chain sequences, identified by the methods disclosed herein are correctly paired, thereby allowing for high-throughput identification antigen-binding antibodies.

In one embodiment, a population of B cells seeded as individual cells into a microwell array are given sufficient time to secrete full length antibodies within their wells for capture on high density magnetic beads coated with the target antigen as well as a capture oligonucleotide that is complementary to the desired transcripts of interest. These beads are retrieved using a magnetic and incubated with a second set of low density polystyrene (or other low density material) coated with Protein G (or other proteins with affinity for full length antibodies in general) for a sufficient period of time. The difference in the total density of the bead complexes (bridged by antigen-specific antibodies) and the non-complexed high density magnetic capture beads is used to enrich for only those magnetic beads that were able to form complexes. The density of the complexed beads is generally lower than the high density beads and they have a low enough settling velocity to remain enriched above a mixture of glycerol and water (of a specified density that is at least lower than the high density magnetic beads but higher or near to the density of bead complexes bridged by antibodies) after centrifugation at high enough speeds to pellet the high density magnetic beads. These enriched beads are then emulsified in RT-PCR mixture and only the mRNA associated with cells that were able to secrete antigen-specific antibodies (above background levels) is amplified and sequenced in high-throughput, allowing for the high-throughput assaying of many cells to specifically enrich for genetic information from those secreting antibodies with an affinity or avidity for the target antigen.

In other embodiments, cells are seeded into individual wells on a microwell array as before, however, non-magnetic high density silica beads coated with target antigen and capture oligonucleotide are seeded into the wells with them and allowed to capture secreted full length antibodies. These beads would then be retrieved from the microwells and incubated instead with magnetic beads coated with Protein G (or other useful molecule with an affinity for full length antibodies) for a sufficient period of time and then pelleted on a magnetic. After washing this pellet, this would effectively remove any beads carrying mRNA without also carrying antigen-specific antibodies, allowing for a magnetic enrichment (as opposed to the previously described non-magnetic enrichment using the differences in densities of the bead complexes). As before, these beads carrying both the genotypic and phenotypic information of interest (i.e. antibodies and mRNA) can be emulsified and undergo RT-PCR and any necessary amplification and sequencing for bioinformatics analysis.

In some embodiments, as will be described in the later Examples, a mild lysis buffer (in some preferred embodiments containing 2% Tween-20) would be preferred for lysing the cells in the microwells so as not to disrupt most antibody:antigen interactions, but still effectively lysing the cell and allowing for mRNA retrieval. Downstream of this, after enriching for the beads carrying the genetic information of antigen-specific cells, a harsher buffer (in some preferred embodiments containing 1% lithium dodecyl sulfate (LiDS) and 5 mM dithiothreitol (DTT)) may be used to remove or disrupt various protein interactions or presence that might inhibit downstream RT-PCR and amplification.

In various embodiments, high-throughput sequencing of the end result overlap-extension (or non-linked transcripts in some potential embodiments) amplicons can be sequenced using various sequencing platform companies including Ion Torrent, Illumina and 454 Life Sciences (Roche).

In some embodiments, the hybrid capture beads carrying target antigen and capture oligonucleotides may utilize specific oligonucleotides for various genes or may comprised of a sequence of about 25 thymine nucleotides to capture all polyadenylated mRNAs from a cell. Likewise, the synthesis of these beads may be accomplished through various means including utilizing the strong interaction between streptavidin and biotin molecules (with streptavidin coated beads and biotinylated antigen and oligonucleotides)

or other various types of conjugation chemistry including NETS-activated and COOH-activated beads with antigen and oligonucleotides that are amine-terminated or contain primary amines that will form covalent bonds to these beads in the presence of catalysts.

In some embodiments microfluidic devices or flow-focusing devices may be used to seed individual cells into single emulsion droplets along with a plurality of simultaneous mRNA and antibody capture agents. The cells may be allowed to secrete full length antibodies until a sufficient concentration has been reached for potential antigen-specific full length antibody binding to the capture agents possessing target antigen. Microfluidic devices may again then be used to fuse emulsion droplets containing lysis buffer (optimized for not disrupting most antigen:antibody interactions) with droplets containing cells to induce cell lysis and mRNA capture in a single-cell manner. These emulsions may then be broken using various methods common in the art and the capture agent population may then be enriched for those carrying antigen-specific antibodies and the desired mRNA from the cells secreting those antibodies using methods previously described and explained in further detail in the examples.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Construction of a High Density Microwell Array

A grid of micropillars (56 um in diameter, 50 um in height) is photolithographically patterned onto a silica wafer using SU-8 photoresist (Fisher Scientific). Sylgard 184 (Dow Corning) monomer is mixed with initiator in a 9:1 ratio and stirred well in a fume hood to make the polydimethylsiloxane (PDMS). The mixture is then degassed under vacuum until no air bubbles can be seen. The mixture is then poured over the silica wafer mold (~6 microwell array molds per wafer) and soft baked at 120 degrees Celsius for 20 minutes. The hardened PDMS is then carefully peeled off of the silica wafer mold, each is microwell array cut to its correct size and then hard baked at 150 degrees Celsius for 20 minutes. These microwell arrays can then plasma etched for 5-15 minutes under vacuum to make the wells more hydrophilic. The arrays are then stored in water until use. Each array has dimensions of about 1 inch by 3 inches and contains about 170,000 wells per array in this example. When the microwell arrays are being prepared for an experiment, they are blocked in 1% bovine serum albumin (BSA) in phosphate buffered saline (PBS) for 30 minutes and then washed three times with deionized water, followed with another wash in just PBS. Excess PBS is allowed to drip off onto filter paper.

Figure 3:
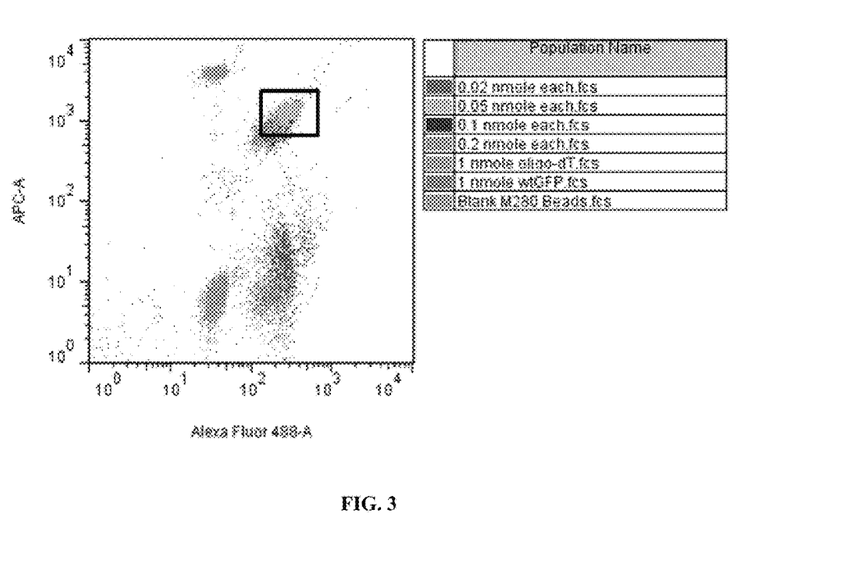
FIG. 3. FACS analysis of various equimolar concentrations of biotinylated oligo-dT(25) and biotinylated wtGFP used for 25 uL of Dynabeads M-280 streptavidin magnetic beads. The Alexa Fluor 488 fluorescence channel detects the presence of wtGFP on each bead, while the APC fluorescence channel detects oligo-dA(25) conjugated to Cy5 fluorophore that was incubated with the synthesized hybrid beads at a higher than theoretical saturation concentration. The results illustrate utilizing 0.05 nanomoles of each constituent with this amount of beads and volume as described in Example 2 was best (under these conditions) for the highest surface densities of each. The population of interest is boxed.

Example 2—Synthesizing Magnetic Beads as Simultaneous mRNA and Antibody Capture Agents In this example, the target antigen (green fluorescent protein as an example) is biotinylated using the EZ-Link Sulfo-NHS-SS-Biotin biotinylation kit (Pierce; Thermo Fisher Scientific) at 100 molar fold (100×) biotin to protein antigen ratio following the kit procedures. Excess biotin is then removed from the mixture by dialyzing for 2 hours in a 10,000 kDa molecular weight cutoff (MWCO) Slide-A-Lyzer Dialysis Cassette in 2 L of 1×PBS. This is repeated twice more and then dialyzed overnight. 5' biotinylated oligo-dT(25) were ordered from Integrated DNA Technologies (IDT). 25 microliters (uL) of Dynabeads M-280 Streptavidin (Invitrogen) were then pelleted on a magnet and resuspended in 25 uL of PBS. 0.05 nanomoles of 100× biotinylated wtGFP antigen and 0.05 nanomoles of 5' biotinylated oligo-dT(25) were then mixed together first, and then that mixture is added to the resuspended M-280 dynabeads, mixed well and allowed to incubate for 30 minutes to 1 hour. The beads were then pelleted on a magnet, washed in 500 uL of PBS and washed twice more in the same manner. They were then resuspended in 500 uL of PBS and stored for future used away from light and at 4 degrees Celsius. Results from the optimization of this example are shown in FIG. 3 along with mixtures of various other equimolar mixtures of antigen and capture oligonucleotide.

Example 3—Designing and Preparing the Overlap Extension PCR Primer Set when Isolating VH:VL Pairs from Cells of Murine, Human and Other Animal B Cell Repertoires Forward primers must first be designed for the VH and VL gene FR1 regions (or leader peptide region) of the V gene families encoded for in the species of interest with an overlap extension set of nucleotides at the 5' end of these primers. The overlap extension region of the VL FR1 (or leader peptide) primers should be complementary to the VH FR1 (or leader peptide) overlap extension region. Likewise, reverse primers must be designed to prime the beginning of each possible constant region of interest. In most cases in the present disclosure, reverse primers specific to the first constant domain of IgM, IgG and IgA, (immunoglobulin kappa) IgK and immunoglobulin lambda (IgL) isotypes are used (however, IgE and IgD may also be used if desired). These reverse primers specific to the constant domains also contain a selected set of nucleotides that constitute an external nucleotide sequence (one unique for heavy chains and one unique for light chains) that is added in through priming and is not complementary to the original transcripts. Primers specific to the external regions are also present, but at a higher concentration of 400 nM to ensure adequate amplification of the full length product.

Figure 2:
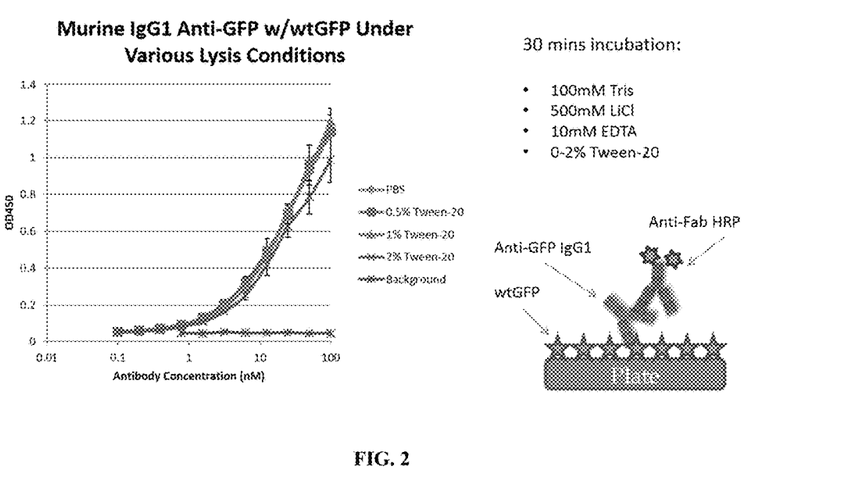
FIG. 2 Results of an enzyme-linked immunosorbent assay (ELISA) depicting the binding of IgG1 antibodies from a murine hybridoma cell line (anti-wtGFP) with affinity for wild type green fluorescent protein (wtGFP) after being incubated in various lysis buffers comprising various concentrations of Tween-20 for 30 minutes. A diagram of the ELISA layout is shown. Results illustrate that various concentrations of Tween-20 in this lysis buffer do not generally disrupt this specific antibody:antigen (anti-wtGFP:wtGFP) interaction.

Example 4—Method for Non-Magnetic Enrichment of Individual Antigen-Specific Linked Transcripts Using Cell Lines A microwell slide array is blocked and washed in PBS as described in Example 1. Hybrid bead capture agents used for the simultaneous capture of mRNA and full length secreted antibodies (herein referred to as simply hybrid beads) are synthesized as described in Example 2. Murine hybridomas secreting full length antibodies (IgG1) with affinity for wtGFP (University of Iowa Developmental Studies Hybridoma Bank) were previously cultured in complete RPMI-1640 supplemented with L-glutamate, sodium pyruvate, penicillin-streptomycin and 10% fetal bovine serum (FBS) to prepare them for analysis. Likewise murine cell line MOPC21 is cultured in the same manner. Both cell lines were passaged every other day and diluted in fresh media in a 1:4 ratio. 1 mL of each type of cell line was pelleted for 5 minutes at 300×g, washed in 1 mL of complete RPMI-1640 and pelleted again for 5 minutes at 300×g. Cells are resuspended and counted. The anti-wtGFP secreting hybridoma cell line is diluted into MOPC21 cells in a 1:4 ratio and 8500 cells from this mixture (cell:well ratio of 1:20; may vary) are seeded onto the washed microwell array and allowed to settle into the wells for 5 minutes. After 5 minutes, the excess medium on the surface is used to gently agitate any unsettled cells and they are given another 5 minutes to settle. This process gentle agitation process was repeated once more. The excess medium is removed and an appropriate number of hybrid capture beads from Example 2, are pelleted and resuspended in 300-400 uL of complete RPMI-1640 and diluted across the top of the microwell array dropwise, leaving about 50 hybrid capture magnetic beads in each well. The microwell array is placed in an incubator at 37 degrees Celsius and 5% $CO_2$ for 3-5 hours while the cells are given time to secrete antibodies to a high enough local concentration. During this time, the secreted full length antibodies from the anti-wtGFP antibody secreting hybridomas bind to the wtGFP bound to the hybrid beads and saturate them, while any non-specific antibodies from the MOPC21 cells do not bind to this antigen on the hybrid beads. After 3-5 hours, any excess medium on the microwell array is removed and a 100 kilodalton (kDa) MWCO membrane (lower MWCO membranes may work as well) that has been cut to fit well over the microwell array (slightly less than 1 inch by 3 inches in both directions) is used to seal the top of the microwell array in a permeable manner. 500 uL of a 2% Tween-20 in 500 mM lithium chloride (LiCl), 100 mM TRIS, 10 mM EDTA lysis buffer is allowed to diffuse through the membrane sealing the wells to induce cellular lysis for 30 minutes. In this manner, polyadenylated mRNA is captured on the hybrid beads to the oligo-dT(25) along with any antigen-specific antibodies. The use of Tween-20 as a nonionic surfactant allows for a mild but effective lysis within 30 minutes, but should generally allow for the retaining of many antibody:antigen interactions (including that of this anti-wtGFP:wtGFP model; see FIG. 2). The hybrid beads are then retrieved from the microwells using a magnet (at 4 degrees Celsius; i.e. cold room) in a buffer of 0.5% Tween-20, 500 mM LiCl, 100 mM TRIS, 10 mM EDTA and then pelleted and washed in 1 ml of a buffer containing 100 mM TRIS, 500 mM LiCl, 1 mM EDTA. The beads were then pelleted and resuspended in 75 uL of PBS. 30 uL of non-magnetic polystyrene beads (or at least in excess of the number of total hybrid magnetic beads being used) coated in Protein G (Spherotech) of diameter 3.2 micrometers are pelleted by centrifugation for 2 minutes at 21,000×g. The protein G beads are then washed in 900 uL of 0.1% Tween-20 in PBS (to very importantly help prevent aggregation) and then pelleted again for 2 minutes at 21,000×g. The protein G beads are then resuspended in 75 uL of PBS and incubated with the 75 uL of collected magnetic hybrid beads for 1 hour. During this time, any beads with wtGFP-specific full length antibodies bound will form complexes with the Protein G beads that have a medium affinity for murine IgG1. This 150 uL mixture is then carefully layered over 400 uL of a 60% freshly made glycerol solution in a 1.5 mL microfuge tube and is centrifuged for 2-3 minutes at 21,000×g. Any beads that were unable to form sufficient complexes with the larger and lower density polystyrene beads pellet at the bottom of the tube or along the back wall below the 60% glycerol/PBS interface. The beads at the interface (all of the protein G beads and some protein G beads in complex with hybrid beads bridged together by anti-wtGFP IgG1 carrying mRNA from those individual cells) are carefully collected with a pipette. The beads are then pelleted on a magnet and washed in 1 ml of a harsh denaturing buffer containing: 1% lithium dodecyl sulfate (LiDS), 5 mM dithiothreitol (DTT), 500 mM LiCl, 100 mM TRIS, and 10 mM EDTA. This removes any protein bound to the mRNA (ribosomes, exon-junction complexes etc.), may inactivate any remaining RNases, as well as may reduce the disulfide bond in the linker holding the antigen to the beads, which may help reduce steric hindrance during the RT-PCR. The beads are then washed again in a 1 ml of a buffer containing 100 mM TRIS, 500 mM LiCl, 1 mM EDTA and then washed in 500 uL of a buffer containing 20 mM TRIS, 50 mM KCl and 3 mM MgCl. The beads are then resuspended in 500 uL of the RT-PCR mixture (115× reaction (~2.85 mL) of One-step Fast QRT-PCR Kit, Rox (Quanta Biosciences)) RT-PCR reagent with the appropriate overlap extension primers as described in Example 3) and then this 500 uL is mixed with the entire RT-PCR mixture and emulsified using an ULTRA-TURRAX Tube Drive Workstation (IKA) in a dropwise manner into an emulsion mixture of 9 mLs 4.5% Span-80, 0.4% Tween-80, 0.05% Triton-X-100 v/v % in mineral oil. This results in one magnetic hybrid bead per emulsion droplet. This emulsion mixture is then placed in 96 well plates with 100 uL in each well and sealed using heat foil and allowed to undergo RT-PCR with the following PCR program for the murine OE primer set: 30 minutes at 55 C followed by 2 minutes at 94° C., followed by four cycles of 94 C for 30 seconds, 50° C. for 30 seconds, 72° C. for 30 seconds, four cycles of 94° C. for 30 seconds, 55° C. for 30 seconds, 72 C for 30 seconds, followed by 32 cycles of 94° C. for 30 seconds, 60° C. for 30 seconds, 72° C. for 30 seconds, followed by a final extension of 72° C. for 7 minutes and then leaving the reaction at 4° C. until ready. The following day, emulsions are then removed from the 96 well plate and pooled and split it microfuge tubes and centrifuged for 10 minutes at 16,000×g. The top oil layer is removed and ~1-1.5 mL of 1:1 isobutanol:water (diethyl ether and chemicals can also be used for emulsion breaking) is added to each tube and vortexed twice for 30 seconds. The tubes are the centrifuged for 1 minute at 16,000×g and the top alcohol layer is removed and discarded. This process is repeated twice more. DNA is then extracted from this aqueous layer using a PCR cleanup kit (Zymo Research). If there is precipitate the sample after isobutanol extraction it is resuspended as best as possible in the provided DNA binding buffer (if the sample still has some precipitate, it can be split into smaller volumes and cleaned up separately to add in resuspension). The DNA from all samples is eluted into a total aggregated volume of 40 uL of deionized water. 0.5 uL of this is then used as template in a nested PCR reaction of 25 uL volume (multiple nested PCRs may be done to increase the final amount of template; Platinum Taq (Invitrogen) is used as the polymerase) with the following PCR program for murine samples: 94 C for 2 minutes following by 4 cycles of 94° C. for 30 s, 60° C. for 30 s, 72° C. for 30 s, followed by usually 31 cycles of 94° C. for 30 s, 62° C. for 30 s, 72° C. for 30 s, followed by a final extension time and temperature of 72 C for 7 minutes and allowing reaction to sit at 4° C. afterwards. The gel extracted product of ~850 bp (VH:VL OE product) is then submitted for high-throughput sequencing using one of the common methods, often the Illumina Miseq 2×250 or 2×300 platforms.

Example 5—Synthesis of Non-Magnetic Beads as Simultaneous mRNA and Antibody Capture Agents Non-magnetic capture agents for simultaneous mRNA and antibody capture can be synthesized in an analogous manner to that described in Example 2. Non-magnetic relatively high density silica beads (Bangs Laboratories) coated with streptavidin (diameters of 0.5-5 um) may be coated with equivalent moles of antigen and 5' biotinylated oligo-dT(25) to allow for efficient mRNA capture and downstream enrichment.

Example 6—Method for Magnetic Enrichment of Transcripts from Cells Secreting Antigen-Specific Antibodies This example demonstrates a similar method of using bead complexes bridged by antibodies for antigen-specific enrichment of genetic information from cells encoding for those antibodies as described in Example 4. However, hybrid mRNA and antibody capture beads used in this example are those described in Example 5. Cells are allowed to secrete antibodies for 3-5 hours as described above, however, when these beads are collected from the microwells after cell lysis, they are washed similarly but incubated instead with an excess number of magnetic Protein G beads (Pierce; Thermo Fisher Scientific) for 1 hour. These bead complexes are then placed over a magnet and any hybrid capture non-magnetic silica beads that do not pellet due to complex formation with the magnetic Protein G beads are washed away with PBS. The pelleted bead complexes are then washed in the harsh 1% LiDS buffer as described in Example 4 and the remainder of the procedure remains the same as in that example.

Example 7—VH:VL Pairing of Expanded Memory B Cells and Other Cell Types and Sources Memory B cells (generally non-secreting or low immunoglobulin secreting cells) are first stimulated in vitro using common methods of cellular expansion, such as by incubation with IL-21, soluble CD40 ligand, anti-APO1 for 4 days (Sendra et al. 2013). The cells resulting from this step are then seeded onto the microwell arrays as previously described. Likewise, cells can be assayed from human and animal patients from blood or other tissues as previously described without immunization or post-immunization such as on Day 6 or Day 7, which are expected by those knowledgeable in the art to have a greater frequency of antigen-specific secreting cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bardelli, M. et al. Ex Vivo Analysis of Human Memory B Lymphocytes Specific for A and B Influenza Hemagglutinin by Polychromatic Flow-Cytometry. PLoS ONE 8, e70620 (2013).

DeKosky, B. J. et al. "High Throughput Determination of the Antibody VH:VL Paired Repertoires," Nat. Biotechnol. 31:166-69 (2013).

DeKosky, B. J. Kojima, T., Rodin, A., Charab, W., Ippolito, Ellington, A. D. and G. Georgiou, "In-depth determination and analysis of the human paired heavy- and light-chain antibody repertoire." Nat. Med. 21, 86-91 (2015).

Georgiou G., Ippolito, G., Beuasang, G., Busse, C. E., Wardemann, H. and S. R. Quake, "The Promise and Challenge of High-throughput Sequencing of the Antibody Repertoire." Nat. Biotechnol. 32:1:58-68 (2014), Krause, J. C. et al. PCR amplification from single DNA molecules on magnetic beads in emulsion: application for high-throughput screening of transcription factor targets, Nucleic Acids Res. 33 (2005).

Love, J. C., Ronan, J. L., Grotenbreg, G. M., van der Veen, A. G. & Ploegh, H. L. A microengraving method for rapid selection of single cells producing antigen-specific antibodies. Nat. Biotechnol. 24, 703-707 (2006).

Mazutis, L. et al. Single-cell analysis and sorting using droplet-based microfluidics. Nat. Protoc. 8, 870-891 (2013).

Ogunniyi, A. O., Story, C. M., Papa, E., Guillen, E. & Love, J. C. Screening individual hybridomas by microengraving to discover monoclonal antibodies. Nat. Protoc. 4, 767-782 (2009).

Reddy, S. T. et al. Monoclonal antibodies isolated without screening by analyzing the variable-gene repertoire of plasma cells. Nat. Biotechnol. 28, 965-U920 (2010).

Sendra, V. G., Lie, A., Romain, G., Agarwal, S. K. & Varadarajan, N. Detection and isolation of auto-reactive human antibodies from primary B cells. Methods 64, 153-159 (2013).

Smith, K. et al. Rapid generation of fully human monoclonal antibodies specific to a vaccinating antigen. Nat. Protoc. 4, 372-384 (2009).

Wu, X et al. Focused Evolution of HIV-1 Neutralizing Antibodies Revealed by Structures and Deep Sequencing. Science 333, 1593-1602 (2011).

What is claimed is:

1. A method for identifying the sequence of two or more transcripts from a plurality of single cells comprising:
   a) incubating isolated single cells and capture agents in individual compartments, wherein the capture agents bind to both mRNA and antibodies;
   b) lysing the isolated cells;
   c) contacting the capture agents, along with bound mRNA and antibodies, with affinity agents that bind to antibodies to form complexes;
   d) purifying the complexes;
   e) performing reverse transcription and PCR amplification on individual complexes to generate linked amplification products comprising two or more cDNAs from said cell; and
   e) sequencing amplification products to identify antibody sequences from a single cell.

2. The method of claim 1, wherein the plurality of single cells comprise a plurality of individual B cells.

3. The method of claim 2, wherein the individual B cells are primary B-cells from a human subject.

4. The method of claim 1, wherein the capture agents are beads.

5. The method of claim 1, wherein the capture agents comprise oligonucleotides which hybridize mRNA.

6. The method of claim 1, wherein said sequencing comprises sequencing antibody VH and VL sequences for an antibody that is bound to an antigen of interest.

7. The method of claim 6, wherein the capture agents comprise the antigen of interest.

8. The method of claim 7, wherein the capture agents are beads that comprise the antigen of interest and a mRNA binding moiety.

9. The method of claim 1, wherein the affinity agents are beads.

10. The method of claim 9, wherein the affinity agents comprise polystyrene beads.

11. The method of claim 9, wherein the affinity agents are magnetic beads.

12. The method of claim 1, wherein the affinity agents have density (mass per unit volume) that is less than the capture agents.

13. The method of claim 1, wherein the affinity agents bind to an antibody constant region.

14. The method of claim 1, wherein the individual compartments are wells in a gel or microtiter plate.

15. The method of claim 1, wherein the compartments are sealed with a permeable membrane prior to lysing the individual cells.

16. The method of claim 1, wherein lysing the isolated cells comprises the use of a mild detergent solution.

17. The method of claim 1, comprising identifying antibody sequences from at least 10,000 individual cells.

18. The method of claim 1, wherein purifying the complexes comprises separating complexes by magnetic properties or by density.

19. The method of claim 1, wherein step (e) comprises performing emulsion-reverse transcription and PCR amplification on individual complexes.

* * * * *